United States Patent [19]

Fuxe

[11] 3,961,060

[45] June 1, 1976

[54] METHOD AND COMPOSITIONS FOR THE TREATMENT OF NEUROLOGICAL DISORDERS

[75] Inventor: Kjell Gunnar Fuxe, Sollentuna, Sweden

[73] Assignee: Astra Lakemedal Aktiebolag, Sodertalje, Sweden

[22] Filed: May 15, 1974

[21] Appl. No.: 469,954

[30] Foreign Application Priority Data

May 17, 1973  Sweden ............................ 73069601

[52] U.S. Cl. ................................ 424/253; 424/319
[51] Int. Cl.² ................. A61K 31/52; A61K 31/195
[58] Field of Search ............................ 424/253, 319

[56] References Cited
UNITED STATES PATENTS 3,646,213   2/1972   Boretholini ......................... 424/319

OTHER PUBLICATIONS

Merck Index 7th Ed. (1960) pp. 187–188.

Chem. Abst, (1) - 74 - 97650a (1971).

Chem. Abst. (2) - 72 - 119941j 1970.

*Primary Examiner*—Stanley J. Friedman
*Attorney, Agent, or Firm*—Gordon W. Hueschen

[57] ABSTRACT

A novel method of treating Parkinsonism, a novel method of treating depressions and a novel method of treating patients who have suffered cerebral strokes, by providing novel pharmaceutical compositions containing a specified fosfodiesterase inhibitor together with a specified known anti-Parkinson agent including dopa, m-tyrosine, apomorphine and ET 495.

26 Claims, No Drawings

METHOD AND COMPOSITIONS FOR THE TREATMENT OF NEUROLOGICAL DISORDERS

The present invention relates to novel synergistic pharmaceutical compositions and to a method for the treatment of certain neurological disorders in mammals including man. More particularly, the invention relates to novel pharmaceutical compositions and a method for alleviating ailments caused by a lower than normal activity in the dopamine systems in the brain. Among such ailments may be mentioned parkinson's disease, which is considered to be a chronic neurological disorder and is characterized i.a. by tremor, rigidity of the limbs, hypokinesia, or abnormally decreased mobility, and akinesia, or abnormal absence or poverty of movements.

The pathophysiology of parkinsonism in man can, at least partly, be explained with a degeneration in the dopaminergic system in the brain, localized to the caudate nucleus, putamen and substantia nigra. These parts of the brain contain in normal human subjects about 80 percent of the total amount of dopamine in the brain. In patients suffering from parkinsonism a depletion of dopamine,

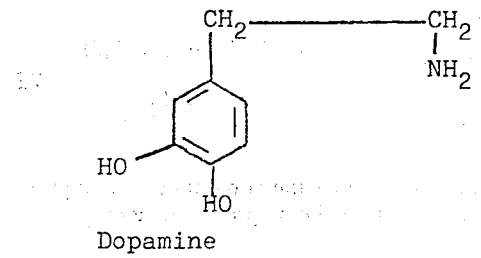

Dopamine in the brain is observed. For treatment of parkinsonism it has been suggested to administer to the patient a compound of the formula

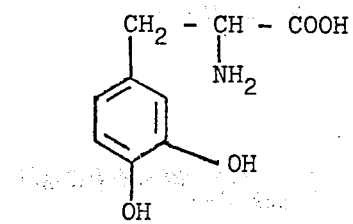

in which formula $R^1$ is H or OH and $R^2$ is H or an alkyl group containing from 1 to 3 carbon atoms. The formula I includes dopa, of the structural formula (ii)

and esters thereof, and m-tyrosine, of the structural formula

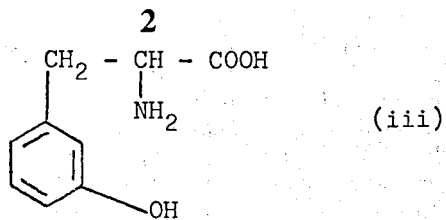

and esters thereof. Illustrative examples of groups $R^2$ are $CH_3$, $C_2H_5$, $CH_2CH_2CH_3$, $CH(CH_3)_2$. Dopa is a precursor of dopamine, which substance does - in contrast to dopamine itself - pass the blood-brain barrier and is decarboxylated in the brain with formation of dopamine. Another method for treatment of parkinsonism which has been tested comprises administration of apomorphine,

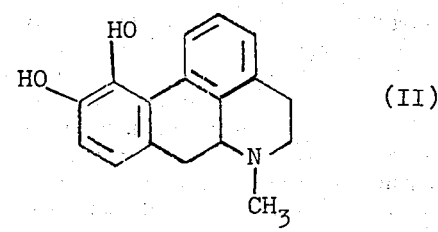

Apomorphine

Apomorphine is a dopaminergic agent which has been tested as an agent for treatment of parkinsonism, see Cotzias et al, The New England Journal of Medicine 282 31–33 (1970). Apomorphine has been found to have an alleviating effect on akinesia and rigidity occurring in connection with Parkinson's disease but its severe drawbacks, mainly the short duration of its desired therapeutic effect and its emetic effect, render the therapeutical use of apomorphine for treatment of parkinsonism practically impossible.

Still another method for treatment of parkinsonism which has been tested (Corrodi et al., European Journal of Phamacology Vol. 20 p. 195–204) comprises administration of the compound 1-(2'-pyrimidinyl)-4 (3'',4''-methylenedioxyphenyl)-piperazine, herebelow denoted ET 495, with the structural formula

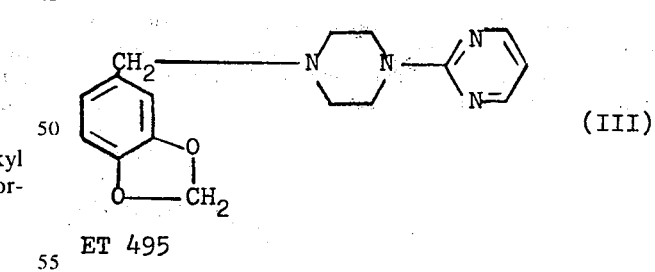

ET 495 or a therapeutically acceptable salt thereof. The compound of the formula (III) is known to have cadiovascular effects, see Laubie et al, European Journal of Pharmacology 6 (1969) 75–82, and it is being used in therapy against various vascular diseases, mainly in the legs. The toxicity of ET 495 is also reported by Laubie et al. loc. cit. The synthesis of the compound is described by Regnier et al., J. Med. Chem. 11, 1151 (1968).

It has been found according to the present invention that the effect of the aforementioned compounds I, II and III including dopa, apomorphine, ET 495, and m-tyrosine on the dopaminergic nerve system can be greatly enhanced and the duration of the effect vastly prolonged by administering a dopaminergic substance selected from the group consisting of the compounds I, II and III including dopa, apomorphine, ET 495, and m-tyrosine, in combination with a fosfodiesterase inhibitor selected from the group consisting of caffeine, teofyllamine and papaverine. Caffeine, teofyllamine and papaverine are all known compounds. Also mixtures of caffeine, teofyllamine and/or papaverine can be used together with a mixture of one or more of the dopaminergic substances. In this way the amounts of the dopaminergic substances which have to be administered in order to achieve the desired therapeutical effect can be minimized while at the same time the duration of the therapeutical effect is prolonged, which is a distinct medicinal advantage. By decreasing the amount of active substance which has to be given to the patients the risk for side effects decreases, resulting in a safer treatment because the gap between the therapeutic dose and the toxic dose is increased.

Thus, the present invention in one aspect provides novel pharmaceutical compositions containing a dopaminergic agent selected from the group consisting of the compounds I, II and III including dopa, apomorphine, ET 495, m-tyrosine, and 1–3 carbon atom alkyl esters of dopa and m-tyrosine, in combination with a fosfodiesterase inhibitor selected from the group consisting of caffeine, teofyllamine and papaverine, normally together with commonly used excipients and diluents. Where applicable, members of both the groups of compounds may be used in the form of a therapeutically acceptable salt. Dosage unit forms of the pharmaceutical preparations may be designed for administration by the oral or parenteral route or by injection.

In another aspect, the present invention provides a method for alleviating ailments caused by a lower than normal activity in the dopamine systems in the brain. In particular, the invention gives an improved method for treating parkinsonism, tha is a method for alleviating the symptoms of rigidity, akinesia and tremor in patients suffering from Parkinson's disease.

The novel compositions according to the present invention may also contain such substances which previously have been shown to improve the effect of dopa, m-tyrosin and other agents in the treatment of parkinsonism. Examples of such compounds are the compounds of the formula

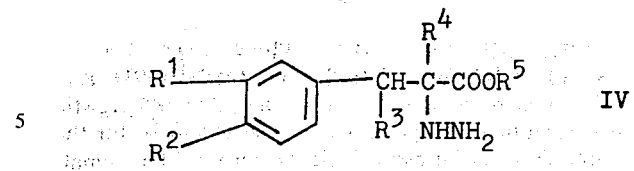

described in French Pat. specification No. 2,081,377, wherein $R_1$ and $R^2$ are H, OH, alkoxy containing 1–6 carbon atoms, $R^3$ and $R^4$ are H or alkyl containing from 1 to 6 carbon atoms, and $R^5$ is H or a metal or an alkyl group containing 1–6 carbon atoms; the compounds of the formula

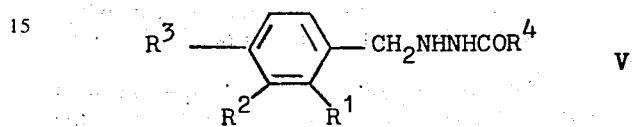

described in the British Pat. specification No. 1,247,073, wherein $R^1$, $R^2$ and $R^3$ are OH or groups convertible to OH, $R^4$ is aminomethyl or a group convertible to aminomethyl; and the compound of the formula

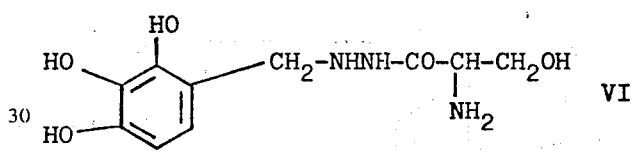

The formula IV includes the compound α-methyl-α-hydrazino-3,4-dihydroxyphenyl propionic acid:

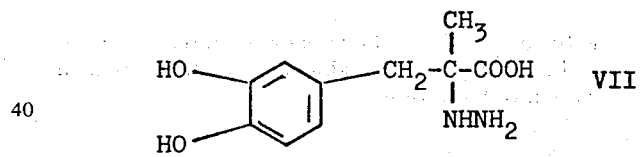

which compound herebelow is denoted with its code number MK 486.

Examples of fosfodiesterase inhibitors which besides caffeine, teofyllamine and papaverine can be used in combination with the compounds I, II and/or III above, are:

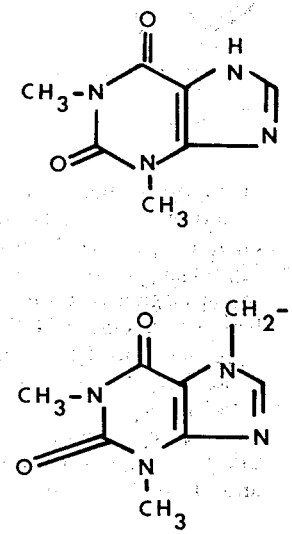

1,3-dimethyl-2,6-dioxo-1,2,3,6-tetrahydropurine (Theophylline)

7-(2,3-dihydroxypropyl)-theophylline

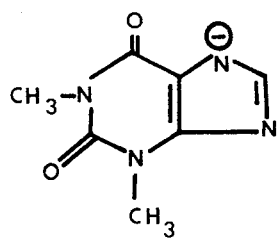 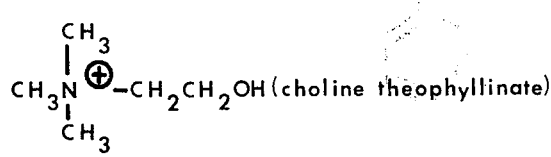 (choline theophyllinate)
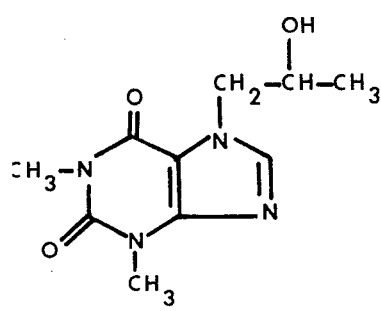 7-(2-hydroxypropyl)-theophylline (Proxyphylline)
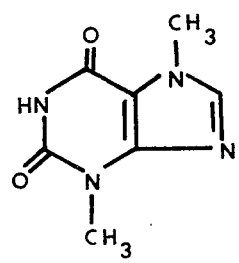 3,7-dimethylxanthine (theobromine)
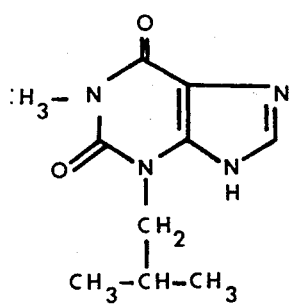
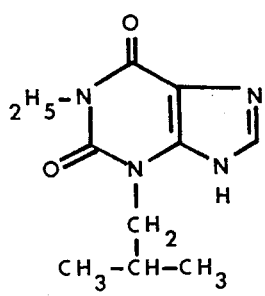
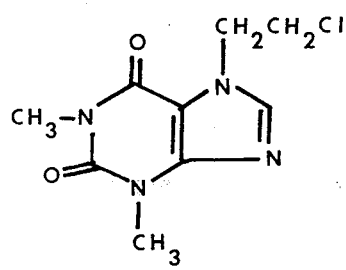 7-(β-chloroethyl)theophylline

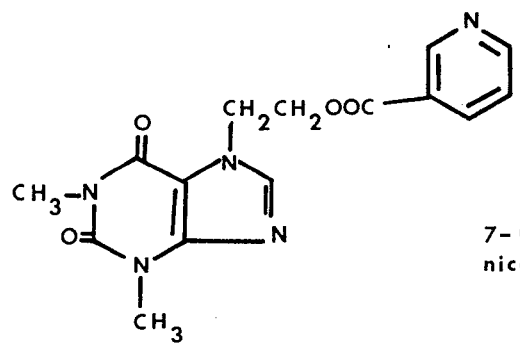
7-(2-hydroxyethyl)theophylline nicotinate
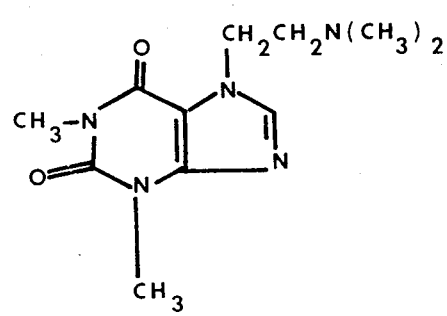
7-(2-dimethylaminoethyl) theophylline
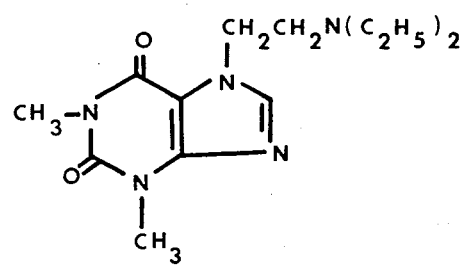
7-(2-diethylaminoethyl) theophylline
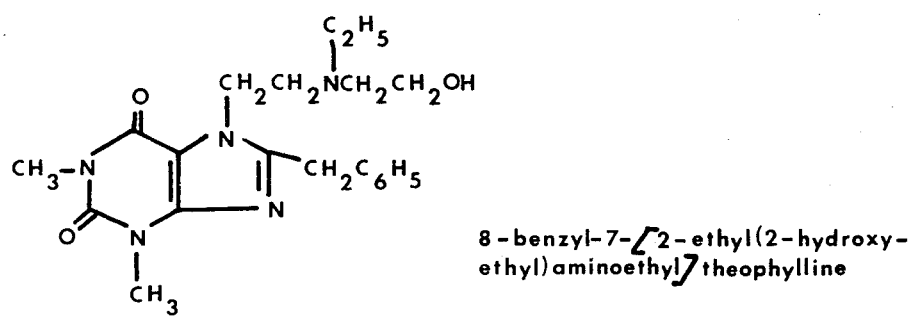
8-benzyl-7-[2-ethyl(2-hydroxy-ethyl)aminoethyl]theophylline
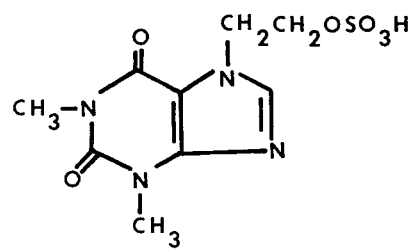
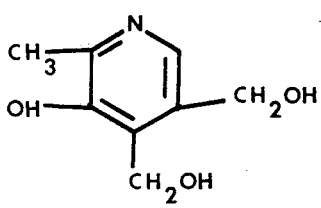
7-(2-hydroxyethyl)theophylline hydrogen sulphate compound with pyridoxol

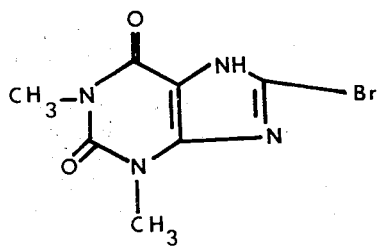 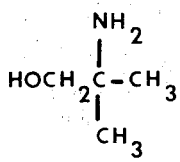

8-bromotheophylline compound with 2-amino-2-methyl-1-propanol

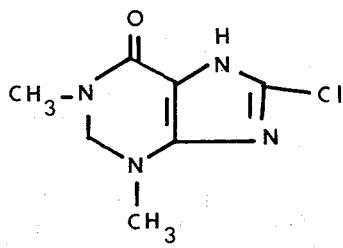

8-chlorotheophylline

Caffeine, theophyllamine and papaverine have the structural formulas

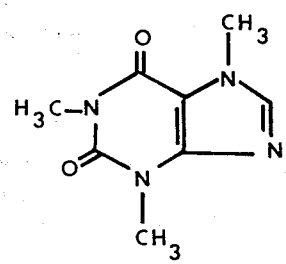

1,3,7-trimethylxanthine

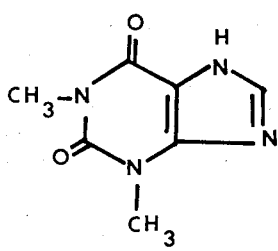 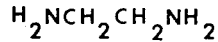

ethylenediaminetheophyllinate

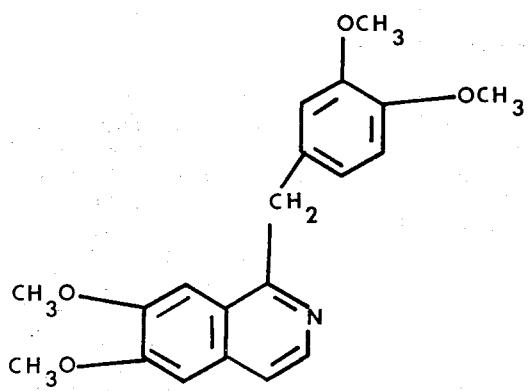

papaverine

Parkinsonism may be characterized not only by a lower than normal activity in the dopamine systems in the brain but also by a degeneration of the noradrenaline neurons in the brain. Thus, also the noradrenaline systems in the brain exhibit in such case a lower than normal activity. Such a state of lower than normal activity in the noradrenergic neurons also characterizes certain states of depression. It has been shown - reference is made to G. C. Palmer, Neuropharmacology Vol. 11 p. 145 (1972) and to Weiss, Strada, Advances in Cyclic Nucleotide Research Vol. 1 p. 357, Raven Press, New York (1972) that the noradrenaline receptors in the brain as well as the dopamine receptors in the brain exert their function via a cyclic AMP (adenosine monophosphate) mechanism. It is therefore concluded that the novel pharmaceutical compositions of the present invention, which affect the dopamine receptors very strongly, also will affect the noradrenaline receptors equally strongly. That the compositions of the invention do have an effect on intact noradrenaline receptors is shown below in the tests on acutely spinalized rats. Since it also is known that the noradrenaline receptors become supersensitive to noradrenergic substanses such as dopa and desipramine when the noradrenaline system is caused to degenerate - reference is made to the above mentioned papers by Palmer and Weiss, Strada - it is clear that the unexpectedly increased effect of the compositions of the invention in the tests in the dopamine model, that is on the turning behaviour of rats, will have a counterpart in an unexpectedly increased effect of the same compositions on a degenerated noradrenaline system, which means, in turn, that the novel compositions of the present invention also provide a new way of treating depressions.

Thus, it is an object of the present invention to provide a method for treating certain types of depressions by administering the novel pharmaceutical compositions according to the invention or the active ingredients thereof, in particular the caffeine-dopa and teofyllamine-dopa combinations with or without the addition of known antidepressants or the imipramine type, such as desipramine, imipramine and protriptyline. The combinations caffeine-desipramine, caffeine-imipramine, caffeine-protriptyline, and teofyllamine-imipramine, and teofyllamine-protriptyline may be mentioned as further useful combinations.

The mentioned antidepressant drugs which are known compounds, have the structural formulas

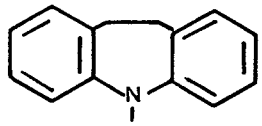 desipramine

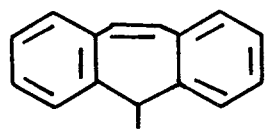 protriptyline

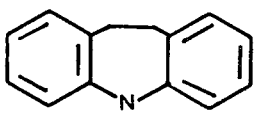 imipramine

Still another area where the compositions of the invention are of potential value is in the treatment of patients who have suffered cerebral strokes. It has been shown in experimental animals - reference is made to Wurtman, Zervas, J. Neurosurg. Vol. 40 p. 34–36 (1974) - that experimentally developed conditions which are similar to the conditions at hand in humans who have suffered strokes lead to a major reduction of the amount of dopamine in the brain, and degeneration of the dopamine system with development of dopamine receptor super-sensitivity. Therefore, it should be a therapeutic advantage in treating such patients with drugs which stimulate the central dopaminergic receptors. The novel compositions of the present invention should cause the same unexpected increase in dopamine receptor activity and therefore be highly useful in such treatment.

The invention also provides, as mentioned above, a novel method for the treatment of depressions by administering a therapeutically effective amount of at least one member of the group consisting of caffeine and teofyllamine in combination with or concurrently with an antidepressant drug of the imipramine type such as desipramine, imipramine and protriptyline, which preferably blocks noradrenaline-uptake. The invention also provides novel pharmaceutical compositions, and a method of their preparation, containing a member of the group consisting of caffeine and teofyllamine in combination with an antidepressant as mentioned above. The pharmaceutical preparations containing caffeine teofyllamine and an antidepressant are prepared in conventional manner analogously as described below.

In a still further aspect of the invention, a method is provided for potentiation of the dopaminergic effect of the compounds I, II and III including dopa, apomorphine, ET 495 and M-tyrosine, and 1–3 carbon atom alkyl esters of dopa and m-tyrosine, by incorporating into a composition containing one or more of said substances a suitable amount of a fosfodiesterase inhibitor selected from the group consisting of caffeine, teofyllamine and papaverine, or administering the active agents concurrently. Methoxylated metabolites, e.g. apocodeine, may be used in place of apomorphine itself, if desired.

In a still further aspect of the invention, a method is provided for treating patients who have suffered a stroke by administering a composition according to the invention.

In clinical practice the novel compositions of the present invention will normally be administered orally, parenterally or by injection in the form of pharmaceutical preparations comprising the active ingredient in the form of the free base or a pharmaceutically acceptable salt thereof, e.g. the hydrochloride, in association with a pharmaceutically acceptable carrier which may be a solid, semi-solid or liquid diluent or as ingestible capsule. Usually the dopaminergic substance and the fosfodiesterase inhibitor will together comprise between about 0.1 and about 95 percent by weight of the preparation, for example, between 0.5 and 20 percent for preparations intended for injection and between 0.1 and 50 percent for preparations intended for oral administration.

To produce pharmaceutical preparations in the form of dosage units for oral application containing a compound of the invention in the form of the free base, or a pharmaceutically acceptable salt thereof, the active ingredients may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine, and also may include lubricants such as magnesium or calcium stearate or a Carbowax or other polyethylen glycol wax and compressed to form tablets or centres for dragees. If dragees are required, the centres may be coated, for example with concentrated sugar solutions which may contain gum arabic, talc and/or titanium dioxide, or alternatively with a lacquer dissolved in easily volatile organic solvents or mixtures of organic solvents. Dyestuffs can be added to these coatings, for example, to distinguish between different contents of active substance. For the preparation of soft gelatine capsules (pearl-shaped closed capsules) consisting of gelatine and, for example, glycerin, or similar closed capsules, the active substances may be admixed with a Carbowax[R]. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid. Dosage units for rectal application may be in the form of suppositorier comprising the active substances in admixture with a neutral fatty base, or gelatine rectal capsules comprising the active substance in admixture with a Carbowax[R] or other polyethylene glycol wax.

Liquid preparations for oral application may be in the form of syrups or suspensions, for example solutions containing from about 0.1 to 20 percent by weight of active substance, sugar and a mixture of ethanol, water, glycerine, propyleneglycol and optionally, aroma, saccharine and/or carboxymethylcellulose as a dispersing agent.

For parenteral application by injection preparations may comprise an aqueous solution of a water soluble pharmaceutically acceptable salt of the active substance desirably in a concentration of 0.5–10 percent by weight and optionally also a stabilising agent and/or buffer substance in aqueous solution. Dosage units of the solution may advantageously be enclosed in ampoules.

The relative amounts dopaminergic substance-fosfodiesterase blocker may vary but the ratios given in Table 1 below may be mentioned as illustrative. The percentages are given in weight percent calculated on the total weight of dopaminergic substance and fosfodiesterase inhibitor.

Dosage units for oral administration preferably contain the following relative amounts of dopaminergic substance and fosfodiesterase inhibitor: Dopa: up to about 400 mg. Any of caffeine, teofyllamine and papaverine: from about 100 to about 1000 mg. ET 495: up to about 40 mg. Any of caffeine, teofyllamine and papaverine: from about 100 to about 1000 mg. Apomorphine: up to about 10 mg. Any of caffeine, teofyllamine and papaverine: from about 100 to about 1000 mg. m-Tyrosine: up to about 1000 mg. Any of caffeine, teofyllamine and papaverine: from about 100 to about 2500 mg.

The amounts given for dopa and m-tyrosine are also valid for the 1–3 carbon atom alkyl esters thereof.

The maximum daily doses of ET 495 when administered without fosfodiesterase inhibitor is about 300 mg at oral administration and about 100 mg at parenteral administration. The maximum daily doses of dopa when administered without fosfodiesterase inhibitor is about 10 g at oral administration. These dosages are upper limits also for the said substances when administered with a fosfodiesterase inhibitor according to the present invention. Use of the novel compositions according to the present application naturally means that these limits need not be fully utilized.

The biological effectiveness of the novel compositions according to the present invention is illustrated in the following.

BIOLOGICAL TESTS

A. Effect on dopamine receptors

One animal model available for the evaluation of central dopaminergic substances is a test on rotation of rats with unilateral lesions in the brain. As described by Ungerstedt (European J. Pharmacology 5, 107 (1968) interruption of the nigroneostriatal dopamine neurons Table 1

| Combination of substances | Examples of relative amounts dopaminergic substance-fosfodiesterase blocker | | | |
|---|---|---|---|---|
| | Percentage range of dopaminergic substance % (w/w) | Preferred amount of dopaminergic substance % (w/w) | Percentage range of fosfodiesterase blocker % (w/w) | Preferred amount of fosfodiesterase blocker % (w/w) |
| Dopa-caffeine | 20–60 | 40 | 80–40 | 60 |
| Dopa-teofyllamine | 20–60 | 40 | 80–40 | 60 |
| Dopa-papaverine | 20–60 | 40 | 80–40 | 60 |
| ET 495-caffeine | 1–10 | 4 | 99–90 | 96 |
| ET 495-teofyllamine | 1–10 | 4 | 99–90 | 96 |
| ET 495-papaverine | 1–10 | 4 | 99–90 | 96 |
| Apomorphine-caffeine | 0.5–5 | 1 | 99.5–95 | 99 |
| Apomorphine-teofyllamine | 0.5–5 | 1 | 99.5–95 | 99 |
| Apomorphine-papaverine | 0.5–5 | 1 | 99.5–95 | 99 |

The figures given for dopa and m-tyrosine are valid also for the 1–3 carbon atom alkyl esters thereof.

Examples of further combinations dopaminergic substance-fosfodiesterase inhibitor are m-tyrosine-caffeine, m-tyrosine-teofyllamine and m-tyrosine-papaverine.

Another way of expressing the information contained in Table I is to say that suitably 2 parts of dopa and 5 parts of any of caffeine, teofyllamine and papaverine suitably are combined; that 1 part of ET 495 and 25 parts of any of caffeine, teofyllamine and papaverine suitably are combined; and that 1 part of apomorphine and 100 parts of any of caffeine, teofyllamine and papaverine suitably are combined. All "parts" are parts by weight.

by injection of 6-hydroxydopamine into the substantia nigra causing a degeneration of the cell bodies of these neurons leads to parkinson-like symptoms in rats. Injection of dopaminergic substances leads to a dose dependant rotation of the animals towards the unoperated side away from the lesion. This rotation can easily be measured and the duration of the effect determined. In this test known substances having a clincally verified antiparkinson action are active. Rats with a unilateral lesion in the left nigro-neostriatal dopamine pathway, produced according to Ungerstedt, loc.cit, were injected intraperitoneally with the test substance and the animal placed in a rotometer where the total number of rotations could be recorded. The test results are summarized in Tables 2–7 below. The letters DA mean "dopaminergic." The letters "s.e.m." mean "standard error of the mean."

Table 2

The effect of caffeine and teofyllamine on the turning behaviour in rats with a unilateral lesion of the nigro-neostriatal DA pathway The drugs were given i.p. and the number of turns were measured in a specially built Rotometer (Ungerstedt and Arbuthnott, Brain Res. 24: 485, 1970). The values (total number of turns) give mean value of six experiments ± s.e.m. Statistical significance according to Student's t-test.

| Treatment | Dose mg/kg | Total number of turns Mean ± s.e.m. |
|---|---|---|
| Caffeine | 50 | 77 ± 16 [a] |
|  | 25 | 227 ± 39 [b] |
|  | 12.5 | 66 ± 11 [c] |
|  | 2.5 | 44 ± 7 |
| Teofyllamine | 100 | 31 ± 5 [d] |
|  | 25 | 465 ± 145 [e] |
|  | 10 | 39 ± 15 [f] | a-b: p <0.001; b-c: p <0.001; d-e: p <0.001; e-f: p <0.001

Table 3

The effect of combined caffeine and dopa treatment on the turning behaviour in rats with a unilateral lesion of the nigro-neostriatal DA system Caffeine was given i.p. as the citrate salt 1 hour before l-dopa injection (i.p.). The values (total number of turns) give mean value of six experiments ± s.e.m.
Statistical significance according to Student's t-test.

| Pretreatment | Dose mg/kg | Treatment | Dose mg/kg | Total number of turns Mean ± s.e.m. |
|---|---|---|---|---|
|  |  | l-dopa | 10 | 50 ± 17 [a] |
| Caffeine | 50 | l-dopa | 10 | 1090 ± 160 [b] |
| Caffeine | 25 | l-dopa | 10 | 1687 ± 171 [c] |
| Caffeine | 12.5 | l-dopa | 10 | 1213 ± 118 [d] |
| Teofyllamine | 10 | l-dopa | 10 | 986 ± 20 [e] |
| Caffeine | 2.5 | l-dopa | 10 | 622 ± 159 [f] |
| Caffeine | 2.5* | l-dopa | 10 | 516 ± 212 [g] |
|  |  | l-dopa | 25 | 2047 ± 145 [h] |
| Caffeine | 50 | l-dopa | 25 | 4302 ± 873 [i] | a-b: p <0.001; a-c: p <0.001; a-d: p <0.001; a-e: p <0.001; a-f: p <0.001; a-g: p <0.05; h-i: p <0.05
*Caffein was given immediately before l-dopa injection

Table 4

The effect of combined teofyllamine and dopa treatment on the turning behaviour in rats with a unilateral lesion of the nigro-neostriatal DA pathway Teofyllamine was given i.p. 1 hour before l-dopa injection. The values (total number of turns) give mean value of six experiments ± s.e.m.
Statistical significance according to Student's t-test.

| Pretreatment | Dose mg/kg | Treatment | Dose mg/kg | Total number of turns Mean ± s.e.m. |
|---|---|---|---|---|
|  |  | l-dopa | 10 | 215 ± 135 [a] |
| Teofyllamine | 100 | l-dopa | 10 | 2160 ± 662 [b] |
| Teofyllamine | 25 | l-dopa | 10 | 1005 ± 291 [c] |
| Teofyllamine* | 25 | l-dopa | 10 | 2602 ± 355 [d] |
| Teofyllamine | 5 | l-dopa | 10 | 365 ± 189 [e] |
| Teofyllamine | 1 | l-dopa | 10 | 110 ± 42 [f] | a-b: <0.01; a-c: <0.05; a-d: p <0.001; a-e: not significant a-f: not significant
*Teofyllamine was given i.p. immediately before l-dopa injection

Table 5

The effect of combined papaverin and 1-dopa treatment on the turning behaviour in rats with a unilateral lesion on the nigro-neostriatal DA pathway Papaverin was given i.p. immediately before l-dopa injection. The values (total number of turns) give mean value of six experiments ± s.e.m. Statistical significance according to Student's t-test.

| Pretreatment | Dose mg/kg | Treatment | Dose mg/kg | Total number of turns Mean ± s.e.m. |
|---|---|---|---|---|
|  |  | l-dopa | 10 | 50 ± 17 [a] |
| Papaverin | 50 | l-dopa | 10 | 342 ± 99 [b] |
| Papaverin | 25 | l-dopa | 10 | 372 ± 54 [c] |
| Papaverin | 10 | l-dopa | 10 | 196 ± 88 [d] | a-b: p <0.01; a-c: p <0.001; a-d: not significant

Table 6

The effect of combined caffeine (teofyllamine, papaverin) and ET 495 treatment on the turning behaviour in rats with a unilateral lesion of the nigro-neostriatal Da pathway Caffeine, teofyllamine and papaverin were given i.p. 15 min before ET 495 (1 mg/kg). In the combination with 5 mg/kg of ET 495, caffeine was given 1 hour before ET 495 and 30 min before pimozide. The values (total number of turns) give mean value of six experiments ± s.e.m. Statistical significance according to Student's t-test.

| Pretreatment | Dose mg/kg | Treatment | Dose mg/kg | Total number of turns Mean ± s.e.m. |
|---|---|---|---|---|
|  |  | ET 495 | 1 | 354 ± 84 [a] |
| Teofyllamine | 25 | ET 495 | 1 | 4264 ± 464 [b] |
| Caffeine | 12.5 | ET 495 | 1 | 1830 ± 471 [c] |
| Papaverine | 25 | ET 495 | 1 | 295 ± 110 |
|  |  | ET 495 | 5 | 1647 ± 299 [d] |
| Caffeine | 50 | ET 495 | 5 | 5885 ± 1668 [e] |
| Pimozide | 1 | ET 495 | 5 | 151 ± 49 [f] |
| Caffeine (50) + pimozide | 1 | ET 495 | 5 | 3772 ± 1956 [g] | a-b: p <0.001; a-c: p <0.01; d-e: p <0.05; d-f: p <0.001; d-g: p <0.05; f-g: p <0.001

Table 7

The effect of combined caffeine (teofyllamine, papaverine) and apomorphine treatment on the turning behaviour in rats with a unilateral lesion of the nigro-neostriatal DA pathway The drugs were given i.p. 15 min before apomorphine (i.p.). The values (total number of turns) give mean value of six experiments ± s.e.m. Statistical significance according to Student's t-test.

| Pretreatment | Dose mg/kg | Treatment | Dose mg/kg | Total no. of turns Mean ± s.e.m. |
|---|---|---|---|---|
|  |  | Apomorphine | 0.25 | 391 ± 94 [a] |
| Caffeine | 50 | Apomorphine | 0.25 | 1752 ± 791 [b] |
| Teofyllamine | 25 | Apomorphine | 0.25 | 1323 ± 147 [c] |
| Papaverine | 25 | Apomorphine | 0.25 | 239 ± 127 | a-b: p <0.05; a-c: p <0.05

Table 8

The effects of caffeine (teofyllamine, papaverine) and 1-m-tyrosine (1-m-tyrosine ethylester) treatment on the turning behaviour in rats with a 6-OH-dopamine induced unilateral lesion of the nigro-neostriatal dopamine pathway Caffeine, teofyllamine and papaverin were given i.p. 15 min before 1-m-tyrosine (50 mg/kg, i.p.) or 1-m-tyrosine ethylester (50 mg/kg, i.p.). The values (total number of turns) give mean value ± s.e.m. Statistical significance according to Student's test.

| Pretreatment | Dose mg/kg | Treatment | Dose mg/kg | Total number of turns Means ± s.e.m. Number of rats in parenthesis |
|---|---|---|---|---|
|  |  | l-m-tyrosine | 100 | 64 ± 27 (6) [a] |
| Caffeine | 25 | l-m-tyrosine | 50 | 859 ± 266 (5) [b] |
| Teofyllamine | 25 | l-m-tyrosine | 50 | 910 ± 337 (5) [c] |
|  |  | l-m-tyrosine ethylester | 50 | 156 ± 65 (3) |
| Caffeine | 25 | l-m-tyrosine ethylester | 50 | 1163 ± 510 (4) |
| Caffeine | 25 | l-m-tyrosine ethylester | 25 | 622 ± 14 (3) |
| Teofyllamine | 25 | l-m-tyrosine ethylester | 50 | 852 ± 503 (8) |

Table 8-continued

The effects of caffeine (teofyllamine, papaverine) and 1-m-tyrosine (1-m-tyrosine ethylester) treatment on the turning behaviour in rats with a 6-OH-dopamine induced unilateral lesion of the nigro-neostriatal dopamine pathway. Caffeine, teofyllamine and papaverin were given i.p. 15 min before 1-m-tyrosine (50 mg/kg, i.p.) or 1-m-tyrosine ethylester (50 mg/kg, i.p.). The values (total number of turns) give mean value ± s.e.m. Statistical significance according to Student's test.

| Pretreatment | Dose mg/kg | Treatment | Dose mg/kg | Total number of turns Means ± s.e.m. Number of rats in parenthesis |
|---|---|---|---|---|
| Papaverine | 25 | 1-m-tyrosine ethylester | 50 | 20 ± 7 (3) | a–b: $p < 0.01$; a–c: $p < 0.05$

Table 9

The effects of caffeine (teofyllamine) on the turning behaviour induced in experimental rats by combined m-tyrosine ethylester and MK 486 treatment A 6-OH-DA induced lesion of the left nigro-neostriatal DA pathway was made according to Ungerstedt (1968). MK 486 (100 mg/kg i.p.) was given 30 minutes before 1-m-tyrosine ethylester (i.p.). Caffeine and teofyllamine were given 15 minutes before 1-m-tyrosine ethylester.

| Pretreatment | Dose mg/kg | Treatment | Dose mg/kg | Total numbers of turns Means ± s.e.m. Number of rats in parenthesis |
|---|---|---|---|---|
| MK 486 | | 1-m-tyrosine ethylester | 5 | 15 ± 2 (6)$^a$ |
| MK 486 | | 1-dopa | 5 | 1467 ± 256 (5)$^b$ |
| MK 486+caffeine | 25 | 1-m-tyrosine ethylester | 5 | 3555 ± 505 (5)$^c$ |
| MK 486+caffeine | 25 | 1-m-tyrosine ethylester | 1 | 1972 ± 945 (6)$^d$ |
| MK 486+caffeine | 25 | 1-m-tyrosine ethylester | 0.5 | 214 ± 74 (5)$^e$ |
| MK 486+teofyllamine | 25 | 1-m-tyrosine ethylester | 5 | 3253 ± 611 (5)$^s$ |

Statistical significance according to Student's t-test.
a–b: $p < 0.001$; a–c: $p < 0.001$; a–d: $p < 0.05$; a–e: $p < 0.05$; a–n: $p < 0.05$

Table 10

The effects of caffeine (teofyllamine) on the turning behaviour induced in experimental rats by combined dopa and MK 486 treatment A 6-OH-DA induced lesion of the left nigro-neostiatal DA pathway was made according to Ungerstedt (1968). MK 486 (100 mg/kg, i.p.) was given 30 minutes before 1-dopa (i.p.) caffeine and teofyllamine was given i.p. 15 minutes before dopa.

| Pretreatment | Dose mg/kg | Treatment | Dose mg/kg | Total no. of turns Means ± s.e.m. Number of rates in parenthesis |
|---|---|---|---|---|
| None | | 1-dopa | 10 | 542 ± 146 (5) |
| MK 486 | | 1-dopa | 5 | 1467 ± 256 (5) |
| MK 486 | | 1-dopa | 1 | 50 ± 14 (6)$^a$ |
| MK 486+teofyllamine | 25 | 1-dopa | 1 | 2401 ± 573 (6)$^b$ |
| MK 486+teofyllaine | 5 | 1-dopa | 1 | 274 ± 114 (5)$^c$ |
| MK 486+caffeine | 25 | 1-dopa | 0.25 | 747 ± 290 (6)$^d$ |

Statistical significance according to Student's t-test.
a–b: $p < 0.01$; a–c: $p < 0.1$; a–d: $p < 0.05$

Table 11

The duration of effect on the novel compositions according to the present invention on the rotational behaviour of rats in comparison to the duration of the dopaminergic substances when used without fosfodiesterase inhibitor is indicated in the following Table. Duration of effect of the dopaminergic substances dopa, ET 495 and apomorphine in combination with caffeine

| Pretreatment | Dose mg/kg | Treatment | Dose mg/kg | Duration of effect h |
|---|---|---|---|---|
| — | | 1-dopa | 10 | 1 |
| Caffeine | | 1-dopa | 10 | 3–5 |
| — | | 1-dopa | 25 | 3 |

Table 11-continued

The duration of effect on the novel compositions according to the present invention on the rotational behaviour of rats in comparison to the duration of the dopaminergic substances when used without fosfodiesterase inhibitor is indicated in the following Table. Duration of effect of the dopaminergic substances dopa, ET 495 and apomorphine in combination with caffeine

| Pretreatment | Dose mg/kg | Treatment | Dose mg/kg | Duration of effect h |
|---|---|---|---|---|
| Caffeine | | 1-dopa | 25 | 15–18 |
| — | | ET 495 | 1 | 1 |
| Caffeine | | ET 495 | 1 | 6–10 |
| — | | ET 495 | 5 | 4–5 |
| Caffeine | | ET 495 | 5 | 10–18 |
| — | | apomorphine | 0.25 | 1.5–2 |
| Caffeine | | apomorphine | 0.25 | 3–6 |

Table 12

Duration of effect on rotational behaviour of the combinations MK 486 + dopa and MK 486 + 1-m-tyrosine ethyl ester with or without caffeine (teofyllamine)

| Pretreatment | Dose mg/kg | Treatment | Dose mg/kg | Duration of effect h |
|---|---|---|---|---|
| | | 1-dopa | 10 | 1 |
| MK 486 | 100 | 1-dopa | 5 | 3–5 |
| MK 486 | 100 | 1-dopa | 1 | none |
| MK 486 (100) + teofyllamine | 25 | 1-dopa | 1 | 4–6 |
| MK 486 (100) + teofyllamine | 5 | 1-dopa | 1 | ½–1 |
| MK 486 (100) + caffeine | 25 | 1-dopa | 0.25 | 1–2 |
| MK 486 | 100 | 1-m-tyrosine ethylester | 5 | none |
| MK 486 (100) + caffeine | 25 | 1-m-tyrosine ethylester | 5 | 5–8 |
| MK 486 (100) + caffeine | 25 | 1-m-tyrosine ethylester | 1 | ½–6 |
| MK 486 (100) + teofyllamine | 25 | 1-m-tyrosine ethylester | 5 | 5–8 |

DISCUSSION OF THE TEST RESULTS ON DOPAMINE RECEPTORS

As is seen in Table 2, the fosfodiesterase inhibitors caffeine and teofyllamine have no significant effect on the number of rotations of the rats except for a slight effect in a dose of 25 mg/kg. In Tables 3 and 4 it is also seen that dopa in the dose 10 mg/kg body weight had no significant effect on the number of rotations. Presence of caffeine or teofyllamine gave a more than 20- fold increase (Table 3) in the number of rotations at the same dose of dopa, 10 mg/kg. Similar effects, although not so pronounced, are seen in Table 5 for the combination dopa-papaverine. The very pronounced potentiation of ET 495 with teofyllamine and caffeine is seen in Table 6. Papaverine did not give the same degree of potentiation. Also apomorphine is strongly potentiated by caffeine and teofyllamine, as is seen in Table 7. The potentiating effect was very clear both when the fosfodiesterase inhibitors were administered 1 hour before the dopaminergic substance was administered and when the inhibitor was administered immediately before the dopaminergic substance was administered.

As is seen in Table 6, the substance pimozide, that is 1-[1-[4,4-bis(p-fluorophenyl)butyl]-4-piperidyl]-2-benzimidazolinone, which substance is a known antipsychoticum, effectively blocks the dopaminergic effect of ET 495. The combination caffeine-ET 495 does, however, as is seen in Table 6, overcome the blocking effect of pimozide on the effect of ET 495 and give a pronounced dopaminergic effect. This means that such parkinsonism that is induced by neuroleptica can be effectively treated with the combination caffeine-ET 495 according to the present invention. Such parkinsonism, which cannot be treated with ET 495 per se because of the blockade of the effect of ET 495 caused by the neurolepticum, may occur for example in psychotic patients who are treated with antipsychotic drugs. This effect achieved by caffeine-ET 495 may also be obtained using cafeine in combination with small doses of any dopa and apomorphine and other compounds included in formula I above.

From the test results given in Tables 9 and 10 it is seen that caffeine and teofyllamine greatly enhance and prolong the activity exerted by the MK 486-dopa and MK 486-m-tyrosine ethyl ester combinations in spite of very low amounts of dopa and m-tyrosine. In Table 9 it is also seen that the m-tyrosine ethyl ester in combination with MK 486 caffeine can be used in dosages which are about the same as the dopa dosages in such combinations. This is important since m-tyrosine or esters thereof normally is less active than dopa.

Those combinations are preferred which contain dopa-MK 486-caffeine
dopa-MK 486-teofyllamine
m-tyrosine ethyl ester MK 486-caffeine
m-tyrosine ethyl ester -MK 486-teofyllamine and corresponding combinations containing substances included in the formulas I, II and III together with MK 486 and caffeine, teofyllamine and papaverine. Of these combinations, the dopa-MK 486-caffeine and m-tyrosine ethyl ester -MK 486-caffeine are preferred. The proportions dopa-MK 486 may in these compositions vary between about 0.2:1 and about 8:1. The proportion dopa-caffeine is from about 1:4 to about 1.5:1. The same proportions are valid for dopa-MK 486-teofyllamine combination and for the corresponding m-tyrosine ethyl ester combinations. The relative dosages of the three components when used in clinical practice will depend on the individual requirements in each case. As examples of specific combinations may be mentioned tablets which contain in addition to the usual carrial ingredients

| I | dopa | 100 mg |
| | MK 486 | 50 mg |
| | caffeine | 300 mg |

-continued

| II | dopa | 100 mg |
| | MK 486 | 50 mg |
| | teofyllamine | 300 mg |
| III | m-tyrosine ethyl ester | 100 mg |
| | MK 486 | 50 mg |
| | caffeine | 300 mg |
| IV | m-tyrosine ethyl ester | 100 mg |
| | MK 486 | 50 mg |
| | teofyllamine | 300 mg |

B. EFFECT ON NORADRENALINE RECEPTORS

The effect of compositions of the invention on intact noradrenaline receptors was tested on acutely spinalized rats by the method described by Anden, Corrodi, Fuxe, Hogfeldt, European Journal of Pharmacology v. 2, p 59 (1967) and by Carlsson, Magnusson, Rosengren, Experientia Vol. 19 p. 359 (1963). In this test an increased effect on the noradrenaline receptors is indicated as an increase in the flexor reflex activity.

Table 13

The effect of teofyllamine and caffeine on the dopa-induced increase in flexor reflex activity after nialamide pretreatment
The rats were acutely spinalized 1 hour before the nialamide injection (100 mg/kg, i.p.). 1-dopa was given i.v. in a dose of 1 mg/kg 2 hour later. Caffeine, teofyllamine and desipramine were given i.p. 30 min before the 1-dopa injection. The flexor reflex activity was semiquantitatively estimated on coded rats:
4 = very strong; 3 = strong; 2 = moderate; 1 = weak; 0 = no activity. Number of rats in parenthesis. Statistical significance according to Tukey's quick test.

| Pretreatment | Dose mg/kg | Treatment | 30 min after dopa | 60 min after dopa |
|---|---|---|---|---|
| Saline | | dopa | 1(2) 2(2)$^a$ | 1(1) 2(3)$^e$ |
| Teofyllamine | 50 | dopa | 3(3)$^b$ | 2(2) 3(1) |
| Teofyllamine | 25 | dopa | ½(1) 2(3) | 1(2) 3(1) |
| Caffeine | 25 | dopa | 3(2) 4(2)$^c$ | 3(4)$^f$ | a-b: $p <0.05$; a-c: $p <0.05$; a-d: $p <0.05$; a-f: $p <0.05$; e-g: $p <0.05$

Table 14

The effect of teofyllamine and caffeine on the protriptyline-induced increase in flexor reflex activity after nialamide pretreatment
The rats were acutely spinalized 1 hour before the nialamide treatment ( 100 mg/kg, i.p.). 2 hour following nialamide, protriptyline was given (25 mg/kg, i.p.). Teofyllamine (50 mg/kg, i.p.) and caffeine (25 mg/kg, i.p.) were given 30 minutes before protriptyline. The strength of the flexor reflex activity was semiquantitatively evaluated: 4 = very strong; 3 = strong; 2 = moderate; 1 = weak; 0 = no activity. Number of animals in parenthesis.
Statistical significance according to Tukey's Quick test.

| Pretreatment | Treatment | Magnitude of increase in flexor reflex Time after protriptyline | |
|---|---|---|---|
| | | 15' | 60' |
| Saline | Saline | 0(4)$^a$ | 0(4) |
| Saline | Protriptyline | ½(1) 1(3)$^b$ | 1(1) 2(1) 3(2) |
| Teofyllamine | Protriptyline | 2(4)$^c$ | 2(1) 3(3) |
| Caffeine | Protriptyline | 2(2) 3(2)$^d$ | 3(4) |
| Teofyllamine | Saline | 0(4) | 0(1) 1(3) | a-b: $p <0.05$; b-c: $p <0.05$; b-d: $p <0.05$

DISCUSSION OF THE RESULTS OF THE TESTS ON NORADRENALINE RECEPTORS

It is seen in Table 13 that teofyllamine increases the effect of dopa on the intact noradrenaline receptors in the test animals. These results show that teofyllamine and caffeine have increased the sensitivity of the noradrenaline receptors for activation by noradrenaline formed at the metabolism of dopa. Similarly it is seen in Table 14 that caffeine and teofyllamine increase the effect of protriptyline on the noradrealine receptors.

These results give experimental support for the conclusion that the compositions of the present invention also exhibit an increased stimulating effect on noradrenaline receptors which means that also ailments caused by lower than normal activity in the noradrenaline neurons such as certain types of depression, especially those where dopamine supersensitivity has developed may be treated with the compositions of the present invention.

The following Examples illustrate how the novel compositions of the present invention can be incorporated in pharmaceutical compositions.

EXAMPLE 1. PREPARATION OF SOFT GELATINE CAPSULES 140 g of dopa and 360 g of caffeine were mixed with 500 g of corn oil whereafter the mixture was filled in soft gelatine capsules, each capsule containing 100 mg of mixture.

EXAMPLE 2. PREPARATION OF SOFT GELATINE CAPSULES

The operation described in Example 1 was repeated using 140 g of dopa and 360 g of teofyllamine instead of dopa and caffeine.

EXAMPLE 3. PREPARATION OF SOFT GELATINE CAPSULES

The operation described in Example 1 was repeated using 140 g of dopa and 360 g of papaverine instead of dopa and caffeine.

EXAMPLE 4. PREPARATION OF TABLETS 16 kg of dopa and 32 kg of caffeine were mixed with 20 kg of silicon dioxide of the trade mark Aerosil, whereafter 45 kg of potato starch and 50 kg of lactose were mixed in and the mixture moistened with a starch paste prepared from 5 kg of potato starch and distilled water, whereafter the mixture was granulated through a sieve. The granulate was dried and sieved whereafter 2 kg of magnesium stearate were mixed in. Finally the mixture was pressed into tablets, each weighing 172 mg.

EXAMPLE 5. PREPARATION OF TABLETS

The operation described in Example 4 was repeated using 2 kg of ET 495 and 48 kg caffeine instead of dopa and caffeine.

EXAMPLE 6. PREPARATION OF TABLETS

The operation described in Example 4 was repeated using 0.5 kg of apomorphine and 49.5 kg of teofyllamine instead of dopa and caffeine.

EXAMPLE 7. PREPARATION OF AN EMULSION 30 g of dopa and 70 g of caffeine were dissolved in 2500 g of peanut oil. From the solution thus obtained, 90 g of Gum Arabic, aroma and colour (q.s.) and 2500 g of water an emulsion was prepared.

EXAMPLE 8. PREPARATION OF A SYRUP 4 g of ET 495 and 96 g of teofyllamine were dissolved in 300 g of 95 percent ethanol where 300 g of glycerol, aroma and colour (q.s.) and water 1000 ml were mixed in. A syrup was thus obtained.

EXAMPLE 9. PREPARATION OF A SOLUTION 30 g of dopa and 70 g of caffeine were dissolved in 2000 g of polyoxyethylene sorbitan monooleate, whereafter aroma and colour (q.s.) and water to 5000 ml were mixed in. A drop solution was thus obtained.

EXAMPLE 10. PREPARATION OF TABLETS

The operation described in Example 4 was repeated using 16 kg α-methyl-α-hydrazino-3,4-dihydroxyphenyl propionic acid as a further ingredient.

EXAMPLE 11. PREPARATION OF TABLETS

The operation described in Example 4 was repeated using 16 kg m-tyrosine ethyl ester and 16 kg α-methyl-α-hydrazino-3,4-dihydroxyphenyl propionic acid instead of the 16 kg dopa.

Where combinations of active agents are referred to herein, the active agents can obviously be administered concurrently, i.e. at or about the same time, as well as together in the same dosage form or unit. Also, where such combinations of active agents are administered in the dosage form or unit usual pharmaceutical carriers are normally included, but may in some cases be omitted, if desired.

I claim:

1. A method for alleviating depression and ailments which are related to a decreased activity of the dopamine system in the brain, comprising concurrently administering to a host in need of such treatment dopa and a dopa-potentiating amount of caffeine, the relative proportions of dopa and caffeine, calculated on a basis of the total weight of dopa and caffeine, being between about twenty to eighty percent by weight of dopa and about eighty to twenty percent by weight of caffeine.

2. A method according to claim 1, wherein an effective amount of alpha-methyl-alpha-hydrazino-3,4-dihydroxyphenyl-propionic acid is administered concurrently with the dopa and caffeine.

3. A method according to claim 1, wherein the active ingredients are administered orally or parenterally in dosage unit form.

4. A method according to claim 1, wherein the active ingredients are administered in combination unit dosage form.

5. A method according to claim 1, wherein the active ingredients are administered in a form including also a pharmaceutically acceptable carrier.

6. A method according to claim 1, wherein the relative proportions of dopa and caffeine administered are about 20 to 60 percent by weight of dopa and about 80 to 40 percent by weight of caffeine, these percentages being calculated on a basis of the total weight of dopa and caffeine.

7. A method according to claim 1, wherein an effective amount of an antidepressant agent is also administered concurrently with the dopa and caffeine.

8. A method according to claim 1, wherein the amount of dopa administered is up to a maximum of about 400 mg per unit oral dose.

9. A method according to claim 1, wherein the amount of caffeine administered is between about 100 and about 1000 mg per unit oral dose.

10. A method according to claim 1, wherein the maximum daily dose of dopa, administered concurrently with the caffeine, is about ten grams orally.

11. A method for potentiating the dopaminergic effect of dopa, characterized in that a dopa-potentiating amount of caffeine is administered to a host concurrently with the dopa, the relative proportions of dopa and caffeine, calculated on a basis of the total weight of dopa and caffeine, being between about twenty to eighty percent by weight of dopa and about eighty to twenty percent by weight of caffeine.

12. A method according to claim 11, wherein the relative proportions of dopa and caffeine are about 20 to 60 percent by weight of dopa and about 80 to 40 percent by weight of caffeine, these percentages being calculated on a basis of the total weight of dopa and caffeine.

13. A method according to claim 11, wherein an effective amount of an antidepressant agent is also administered concurrently with the dopa and caffeine.

14. A method for potentiating the dopaminergic effect of dopa, characterized in that dopa is administered to a host in the form of a composition containing a dopa-potentiating amount of caffeine, the relative proportions of dopa and caffeine, calculated on a basis of the total weight of dopa and caffeine, being between about twenty to eighty percent by weight of dopa and about eighty to twenty percent by weight of caffeine.

15. A method according to claim 14, wherein the relative proportions of dopa and caffeine in the composition are about 20 to 60 percent by weight of dopa and about 80 to 40 percent by weight of caffeine, these percentages being calculated on a basis of the total weight of dopa and caffeine.

16. A method according to claim 15, wherein the composition includes a pharmaceutically acceptable carrier.

17. A method according to claim 14, wherein an effective amount of an antidepressant agent is also administered concurrently with the dopa and caffeine.

18. A composition suitable for alleviating depression and ailments which are related to a decreased activity of the dopamine system in the brain, comprising dopa and a dopa-potentiating amount of caffeine, the relative proportions of dopa and caffeine, calculated on a basis of the total weight of dopa and caffeine, being between about twenty to eighty percent by weight of dopa and about eighty to twenty percent by weight of caffeine.

19. A composition according to claim 18, adapted to be administered orally or parenterally in dosage unit form.

20. A composition according to claim 18, which comprises an effective amount of alpha-methyl-alpha-hydrazino-3,4-dihydroxyphenylpropionic acid in addition to the dopa and caffeine.

21. A composition according to claim 20, wherein all of the active ingredients are present in a single combination dosage form.

22. A composition according to claim 18, wherein a pharmaceutically-acceptable carrier is also present.

23. A composition according to claim 18, wherein the relative proportions of dopa and caffeine present therein are about 20 to 60 percent by weight of dopa and about 80 to 40 percent by weight of caffeine, these percentages being calculated on a basis of the total weight of dopa and caffeine.

24. A composition according to claim 18, wherein an effective amount of an antidepressant agent is also administered concurrently with the dopa and caffeine in said composition.

25. A method for the treatment of depression characterized in administering to a host in need of such treatment of a therapeutically effective amount of a pharmaceutical preparation according to claim 24 together with an antidepressant drug of the imipramine type which blocks noradrenaline uptake.

26. A method according to claim 25 wherein the antidepressant drug is selected from the group consisting of desipramine, protriptyline and imipramine.

* * * * *

UNITED STATES PATENT OFFICE
CERTIFICATE OF CORRECTION

Patent No. 3,961,060     Dated  June 1, 1976

Inventor(s) Kjell Gunnar Fuxe

It is certified that error appears in the above-identified patent and that said Letters Patent are hereby corrected as shown below:

Col. 17, Table 9, Line 39:

"a-n:p<0.05"

Page 21, Line 3:

--- a-f:p<0.05 ---

Col. 17, Line 48 (In table 10):

"Number of rates in parenthesis"

Page 21, Line 3 (In table 10):

--- Number of rats in parenthesis ---

Signed and Sealed this

Fourteenth Day of December 1976

[SEAL]

Attest:

RUTH C. MASON
Attesting Officer

C. MARSHALL DANN
Commissioner of Patents and Trademarks